(12) United States Patent
Swanson

(10) Patent No.: US 7,306,589 B2
(45) Date of Patent: Dec. 11, 2007

(54) THERAPEUTIC APPARATUS HAVING INSULATED REGION AT THE INSERTION AREA

(75) Inventor: David K. Swanson, Campbell, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 11/251,578

(22) Filed: Oct. 14, 2005

(65) Prior Publication Data

US 2006/0089630 A1 Apr. 27, 2006

Related U.S. Application Data

(63) Continuation of application No. 10/423,627, filed on Apr. 24, 2003, now abandoned.

(51) Int. Cl.
A61B 18/02 (2006.01)

(52) U.S. Cl. .......................... 606/21; 606/20

(58) Field of Classification Search ............ 606/20–32; 604/96.01–101.01; 607/104–105
See application file for complete search history.

(56) References Cited

U.S. PATENT DOCUMENTS

| | | |
|---|---|---|
| 4,802,475 A | 2/1989 | Weshahy |
| 5,108,390 A | 4/1992 | Potocky et al. |
| 5,147,355 A | 9/1992 | Friedman et al. |
| 5,254,116 A | 10/1993 | Baust et al. |
| 5,261,906 A | 11/1993 | Pennino et al. |
| 5,275,595 A | 1/1994 | Dobak |
| 5,423,807 A | 6/1995 | Milder |
| 5,501,681 A | 3/1996 | Neuwirth et al. |
| 5,634,937 A | 6/1997 | Mollenauer et al. |
| 5,733,280 A | 3/1998 | Avitall |
| 5,807,391 A | 9/1998 | Wijkamp |
| 5,868,735 A | 2/1999 | Lafontaine |
| 5,951,546 A | 9/1999 | Lorentzen |
| 5,971,979 A | 10/1999 | Joye et al. |
| 6,024,740 A | 2/2000 | Lesh et al. |
| 6,039,730 A * | 3/2000 | Rabin et al. ............. 606/23 |
| 6,042,559 A | 3/2000 | Dobak |
| 6,064,914 A | 5/2000 | Trachtenberg |
| 6,074,412 A | 6/2000 | Mikus et al. |
| 6,149,677 A | 11/2000 | Dobak |
| 6,159,207 A | 12/2000 | Yoon |
| 6,231,595 B1 | 5/2001 | Dobak |
| 6,237,355 B1 | 5/2001 | Li |
| 6,241,718 B1 | 6/2001 | Arless et al. |
| 6,241,722 B1 | 6/2001 | Dobak et al. |
| 6,280,439 B1 | 8/2001 | Martin et al. |
| 6,283,959 B1 | 9/2001 | Lalonde et al. |
| 6,290,696 B1 | 9/2001 | Lafontaine |
| 6,355,029 B1 | 3/2002 | Joye et al. |
| 6,379,348 B1 | 4/2002 | Onik |
| 6,409,747 B1 | 6/2002 | Gobin et al. |
| 6,428,534 B1 | 8/2002 | Joye et al. |
| 6,428,563 B1 | 8/2002 | Keller |

(Continued)

FOREIGN PATENT DOCUMENTS

WO WO-02/064070 A1 8/2002

(Continued)

Primary Examiner—Henry M Johnson, III
(74) Attorney, Agent, or Firm—Henricks, Slavin & Holmes LLP

(57) ABSTRACT

Apparatus and methods for insulating tissue during therapeutic procedures.

14 Claims, 7 Drawing Sheets

U.S. PATENT DOCUMENTS

| | | |
|---|---|---|
| 6,432,102 B2 | 8/2002 | Joye et al. |
| 6,443,947 B1 | 9/2002 | Marko et al. |
| 6,468,297 B1 | 10/2002 | Williams et al. |
| 6,494,844 B1 | 12/2002 | Van Bladel et al. |
| 6,517,533 B1 | 12/2002 | Swaminathan |
| 6,514,245 B1 | 2/2003 | Williams et al. |
| 6,547,784 B1 | 4/2003 | Thompson et al. |
| 6,551,274 B2 | 4/2003 | Heiner |
| 6,575,933 B1 | 6/2003 | Wittenberger et al. |
| 6,595,988 B2 | 7/2003 | Wittenberger et al. |
| 6,602,246 B1 | 8/2003 | Joye et al. |
| 6,648,879 B2 | 11/2003 | Joye et al. |
| 6,666,858 B2 | 12/2003 | Lafontaine |
| 6,673,066 B2 | 1/2004 | Werneth |
| 6,709,431 B2 | 3/2004 | Lafontaine |
| 6,786,902 B1 * | 9/2004 | Rabin et al. .................. 606/23 |
| 7,101,387 B2 | 9/2006 | Garabedian et al. |
| 2001/0007951 A1 | 7/2001 | Dobak |
| 2002/0019627 A1 | 2/2002 | Maguire |

FOREIGN PATENT DOCUMENTS

| | | |
|---|---|---|
| WO | WO-03/020334 A2 | 3/2003 |

* cited by examiner

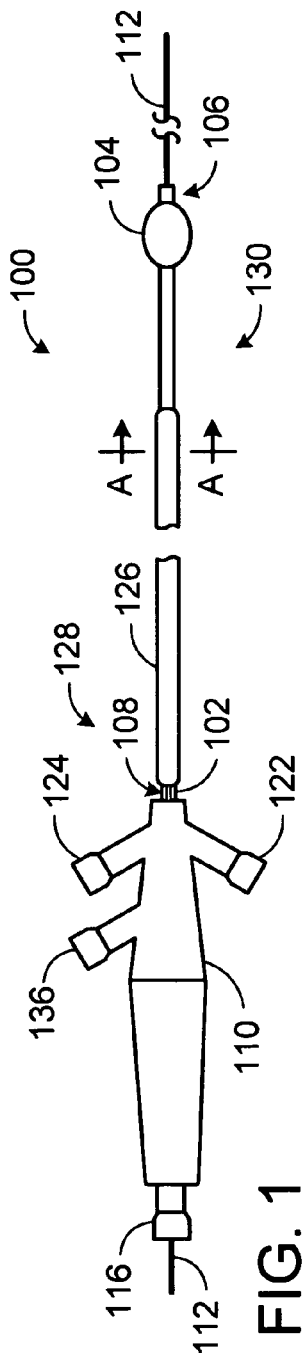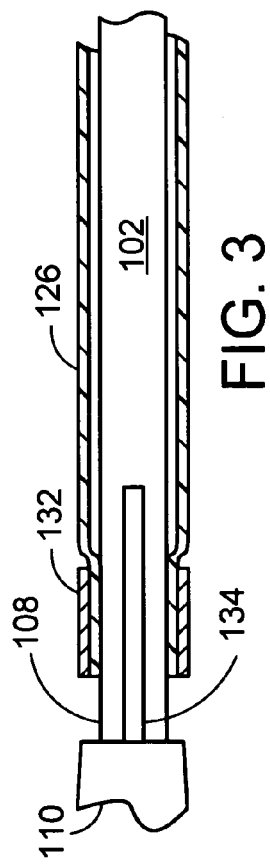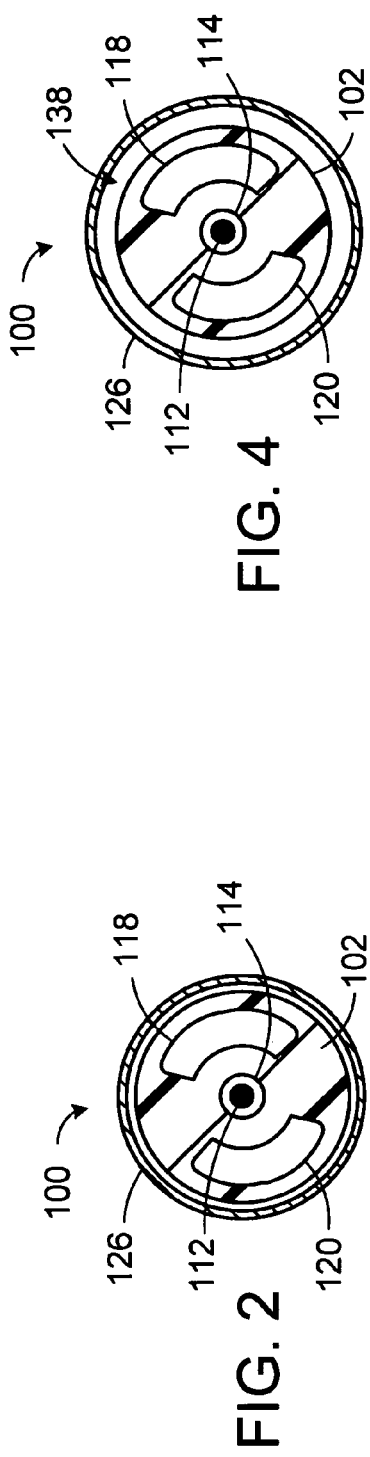

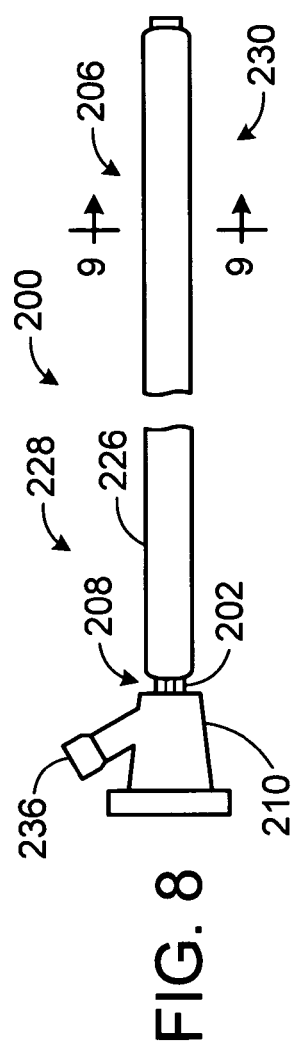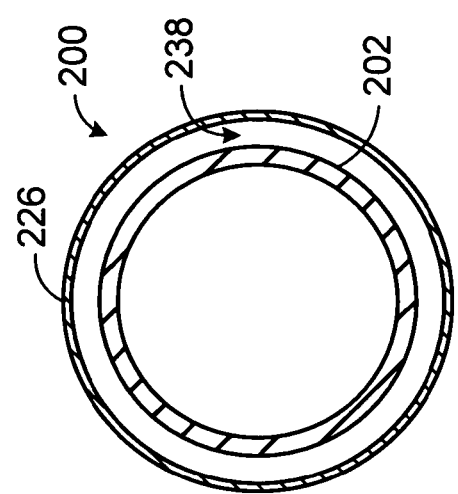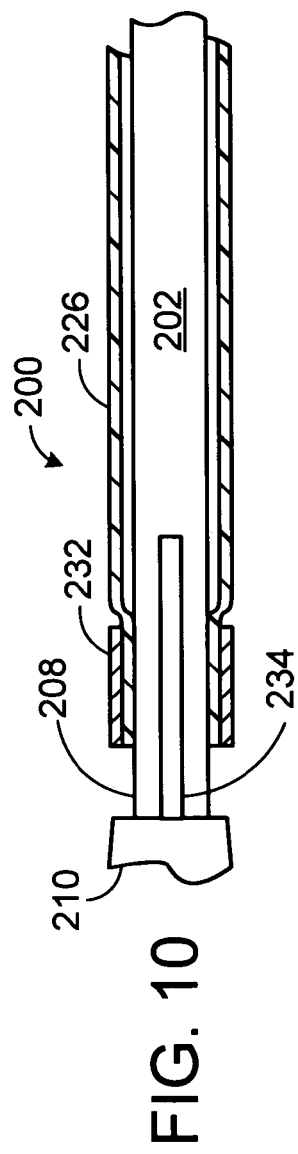

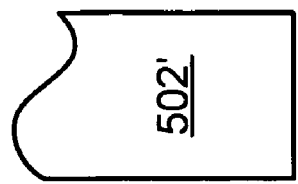
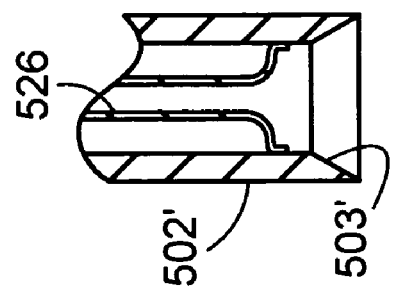
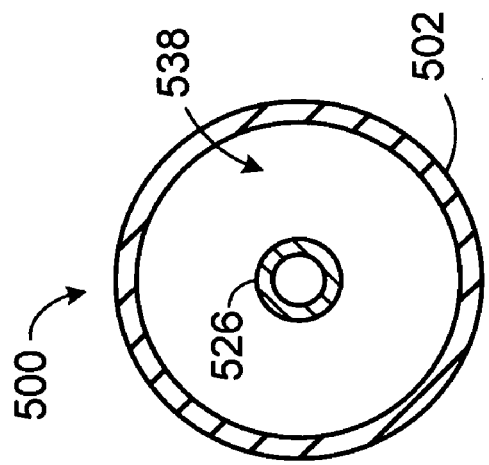
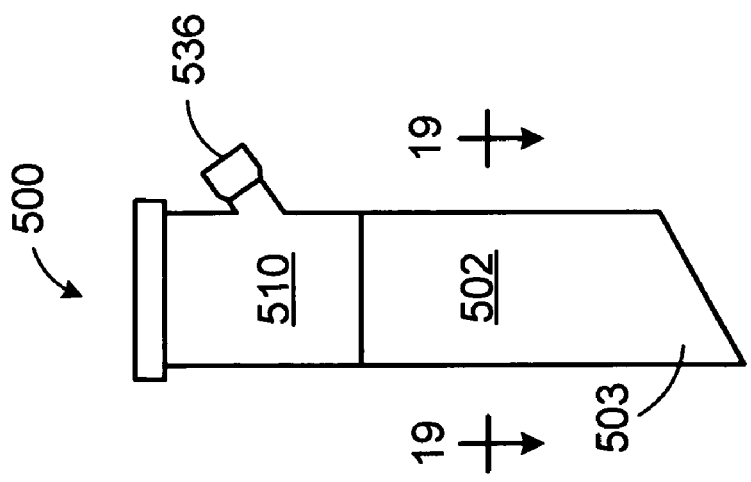

THERAPEUTIC APPARATUS HAVING INSULATED REGION AT THE INSERTION AREA

CROSS-REFERENCE TO RELATED APPLICATIONS

This application is a continuation of U.S. application Ser. No. 10/423,627, filed Apr. 24, 2003, which is incorporated herein by reference, now abandoned.

BACKGROUND OF THE INVENTIONS

1. Field of Inventions

The present inventions relate generally to devices for performing therapeutic operations on body tissue.

2. Description of the Related Art

There are many instances where therapeutic elements must be positioned adjacent to body tissue. One instance involves the formation of therapeutic lesions to the treat cardiac conditions such as atrial fibrillation, atrial flutter and arrhythmia. Therapeutic lesions, which may also be used to treat conditions in other regions of the body such as the prostate, liver, brain, gall bladder, uterus and other solid organs, are typically formed by ablating tissue.

Cryogenic cooling devices are one example of the devices that have been used to form lesions in tissue. During the cryo-ablation of soft tissue (i.e. tissue other than blood, bone and connective tissue), ice crystals disrupt cell and organelle membranes and it is the disruption that kills the tissue. A cryogenic element, such as a balloon or hollow metal tip, is carried on the distal end of a catheter or surgical probe (referred to herein collectively as "probes"), placed in contact with tissue and cooled to a temperature that will cause tissue death. The cryogenic element may be cooled by a variety of techniques. One technique employs the Joule-Thompson ("JT") effect. Here, cryogenic cooling occurs as a result of a rapid decrease of gas pressure that occurs within the therapeutic element. Pressurized cryogenic fluid, such as liquid nitrous oxide, is directed into the therapeutic element where it undergoes rapid phase change and a rapid expansion of the gas from a high-pressure to a lower pressure state. The reaction is endothermic and produces temperatures as low as minus 70° C. at the therapeutic element. In some instances, the cryogenic fluid is pre-cooled in order to increase the cooling power delivered to the targeted tissue. The cryogenic element may also be cooled by directing super-cooled fluid through the catheter or surgical probe to the cryogenic element. Here, the temperature at the therapeutic element can be as low as minus 100° C. when it enters the patient.

The present inventor has determined that conventional cryogenic cooling devices are susceptible to improvement. For example, the present inventor has determined that conventional cryogenic cooling devices can damage tissue at the insertion area, i.e. the area at which the probe is inserted into the patient. In the context of cryogenic probes, which utilize the JT effect, the tissue in the insertion area may be damaged by the nitrous oxide as it returns to the proximal end of probe in its extremely cold gaseous state. Super-cooled fluid, on the other hand, is more likely to damage tissue in the insertion area as it enters the patient. The insertion area, and the tissue contained therein, will vary from procedure to procedure. In the context of cardiovascular therapies which require a catheter to be passed through the femoral vein to a chamber within the heart, for example, the insertion area would include the tissue between the outer surface of the patient's thigh and the femoral vein. With respect to surgical probes, conventional cryogenic cooling devices can damage tissue at the insertion area, i.e. the area at which the probe is inserted into the patient, especially in minimally invasive procedures, in a manner similar to that observed with percutaneous catheter procedures. The proximal or mid-portion of the surgical cryogenic probes can also freeze soft tissues not intended to be ablated. For example, lung tissue can be unintentionally damaged when heart tissue is targeted. When liver tumors are targeted for cryo-ablation, the abdominal wall, spleen, pancreas or stomach could be injured.

BRIEF DESCRIPTION OF THE DRAWINGS

Detailed description of preferred embodiments of the inventions will be made with reference to the accompanying drawings.

FIG. 1 is a plan view of a probe in accordance with a preferred embodiment of a present invention.

FIG. 2 is a section view taken along line A-A in FIG. 1 with the inflatable insulation device in a deflated state.

FIG. 3 is an enlarged, partial section view of a portion of the probe illustrated in FIG. 1.

FIG. 4 is a section view taken along line A-A in FIG. 1 with the inflatable insulation device in an inflated state.

FIG. 8 a plan view of an introducer sheath in accordance with a preferred embodiment of a present invention in an inflated state.

FIG. 9 is a section view take along line 9-9 in FIG. 8.

FIG. 10 is an enlarged, partial section view of a portion of the introducer sheath illustrated in FIG. 8.

FIG. 18 is a front view of an introducer port in accordance with a preferred embodiment of a present invention.

FIG. 19 is a section view take along line 19-19 in FIG. 18.

FIG. 20 is a front view of a portion of a portion of trocar sleeve in accordance with a preferred embodiment of a present invention.

FIG. 21 is a section view of the portion of a trocar sleeve illustrated in FIG. 20.

DETAILED DESCRIPTION OF THE PREFERRED EMBODIMENTS

Figure 6:
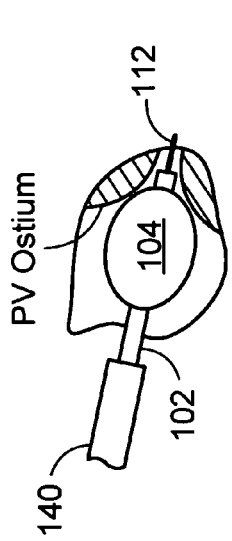
FIG. 6 is side view showing the distal portion of the probe illustrated in FIG. 1 adjacent to a pulmonary vein.

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:

I. Introduction
  II. Exemplary Insulated Catheter
  III. Exemplary Insulated Introducer Sheath
  IV. Exemplary Insulated Surgical Probe
  V. Exemplary Insulated Introducer Ports
  VI. Exemplary Trocars The section titles and overall organization of the present detailed description are for the purpose of convenience only and are not intended to limit the present inventions.

I. Introduction

This specification discloses a number of structures, mainly in the context of cardiac treatment, because the structures are well suited for use with myocardial tissue. Nevertheless, it should be appreciated that the structures are applicable for use in therapies involving other types of soft tissue. For example, various aspects of the present inventions have applications in procedures concerning other regions of the body such as the prostate, liver, brain, gall bladder, uterus and other solid organs. The inventions herein are also applicable to catheter-based probes, surgical probes, introducer sheaths, introducer ports, trocars and other devices that may be inserted into the body. Additionally, although the preferred embodiments of the inventions are described in the context of cryogenic therapies, the inventions are not limited to cryogenic applications. Other applications where thermal insulation is required, such as devices that provide hyperthermic treatments for tumors, or devices that ablate tissue by thermal conduction from hot balloons, are also contemplated. Protection from hot circulating fluids is also required in devices that must be cooled to be safely operated within the body. One example of such a device is a laser ablation device.

Catheter-based probes used to create lesions typically include a relatively long and flexible catheter body that supports a cryogenic element at or near its distal end. The portion of the catheter body that is inserted into the patient is typically from 60 to 140 cm in length and there may be another 20 to 40 cm, including a handle, outside the patient. The length and flexibility of the catheter body allow the catheter to be inserted into a main vein or artery (typically the femoral vein) and directed into the interior of the heart such that the cryogenic element contacts the tissue that is to be ablated. Fluoroscopic imaging is used to provide the physician with a visual indication of the location of the catheter.

Surgical probes, on the other hand, are configured such that the distal end of a surgical probe may be placed directly in contact with the targeted tissue area by a physician during a surgical procedure, such as open-heart surgery. Here, access may be obtained by way of a thoracotomy, median sternotomy, or thoracostomy. Exemplary surgical probes are disclosed in U.S. Pat. No. 6,142,994, which is incorporated herein by reference. Surgical probes preferably include a handle and a relatively short shaft that supports a cryogenic element at or near the distal end.

Introducer sheaths and introducer ports are used to introduce catheters and surgical probes into the body. Introducer sheaths have a relatively long body that may extend through the insertion area to the target tissue region, while introducer ports tend to be relatively short and extend only a short distance beyond the insertion area. Trocars are sharp instruments used to puncture a body cavity and are typically adapted to be used together with a obturator. Once the body cavity has been punctured by the obturator and trocar sleeve (sometimes referred to as a "cannula"), the obturator is removed from the trocar sleeve, thereby leaving the trocar sleeve extending into the body cavity. Surgical procedures are then performed through the trocar sleeve.

Catheters, surgical probes, introducer sheaths, introducer ports and trocars each have a "working length," which is the portion of the device that is inserted into the patient during a procedure, and a "non-working length," which is the portion of the device that remains outside the patient during the procedure. In other words, the non-working length is the portion of the device that will not enter the insertion area. The non-working lengths for catheter and sheath bodies are typically about 10 cm to about 50 cm, while the non-working length for a surgical probe shaft is typically about 10 cm to about 40 cm, and the non-working length for an introducer port is typically about 2 cm to about 10 cm and the non-working length for a trocar is typically about 1 cm to about 2 cm. The length of the insertion area will, of course, vary from procedure to procedure. In those instances where a catheter is inserted through the patient's thigh and into the femoral vein, the insertion area will typically be about 4 cm to about 15 cm in length, because the catheter is deployed at an acute angle. Alternatively, in those instances where a surgical probe is deployed in the directly into the chest by way of a mini-thoracotomy, the insertion area will typically be about 3 cm to about 10 cm in length.

The present apparatus and methods may be used to provide insulation between catheters and surgical probes and, at a minimum, the tissue in the insertion area. In some embodiments, the insulation is provided by an inflatable insulation device. There are a number of advantages associated with such apparatus and methods. For example, in those instances where a probe is used to transport extremely low temperature fluids to and/or from a cryogenic element, the insulation will protect the tissue in the insertion area. The insulation may also be extended distally if desired in order to protect other tissue and/or improve the thermal efficiency of the overall cryogenic system.

II. Exemplary Insulated Catheter

A catheter 100 in accordance with a preferred embodiment of a present invention is illustrated in FIGS. 1-7. The illustrated embodiment includes a elongate catheter body 102 and an inflatable cryogenic element 104 carried on the distal portion 106 of the catheter body. The proximal portion 108 of the catheter body 102 is secured to a handle 110. The exemplary catheter 100 is a non-steerable catheter and is configured to be advanced over a guidewire 112 to the target location. More specifically, the catheter body 102 is provided with a guidewire lumen 114 and the handle 110 is provided with a guidewire port 116 and an internal guidewire lumen (not shown). Thus, once the distal end of the guidewire 112 has been positioned at the target tissue location, the catheter 100 may be advanced over the guidewire to the target tissue location.

In addition to the guidewire lumen 112, the exemplary catheter body 102 includes an infusion lumen 118 and a ventilation lumen 120. The distal ends of the infusion and ventilation lumens 118 and 120 terminate at respective openings (not shown) on the exterior surface of the catheter body that are located within the cryogenic element 104. The proximal ends of the infusion and ventilation lumens 118 and 120 are connected to infusion and ventilation lumen ports 122 and 124 on the handle 110. Suitable infusion and ventilation lumen ports usually includes high-pressure connectors that withstand pressures of at least 100 PSI. Depending on the type of cryogenic cooling that is desired, the infusion and ventilation lumens 118 and 120 may be used to supply and ventilate super-cooled fluid, such as liquid perfluorocarbon that has been cooled to a suitably low temperature such as minus 90° C., or to supply liquid nitrous oxide and ventilate the gas that results from the expansion within the cryogenic element 104. The gas is typically about minus 50° C. when it reaches the proximal end of the catheter body 102.

In order to protect non-target tissue generally, and the tissue associated with the insertion area in particular, the exemplary catheter 100 also includes an inflatable insulation device 126 that is carried on the exterior surface of the catheter body 102. The inflatable insulation device 126 preferably extends distally from a location in close proximity to the distal end of the handle 110, over the non-working length 128 of the catheter body and along at least the proximal area of the working length 130. This will insure that a portion of the inflatable insulation device 126 will be coextensive with the insertion area during use, as is described below with reference to FIG. 5. In the exemplary embodiment illustrated in FIGS. 1-7, the inflatable insulation device 126 extends from a location in close proximity to the handle 110 to a location in spaced relation to the inflatable cryogenic element 104.

As illustrated in FIG. 3, the exemplary inflatable insulation device 126 may be formed by securing a tubular length of material to the exterior of the catheter body 102. In those instances where the insulation device material is from the same class of materials as the catheter body material, thermal bonding may be employed. Adhesive bonding is another suitable technique. In either case, anchors 132 may be positioned on the longitudinal ends of the inflatable insulation device 126 in order to prevent leakage. Gas may be infused into inflatable insulation device 126 by way of a small tube 134, which is carried on the exterior of the catheter body 102 and connected to a gas port 136 on the handle 110. Suitable gas ports include luer lock stopcocks. The gas may also be ventilated from the inflatable insulation device 126 by way of the tube 134 and gas port 136. The outer diameter of the inflatable insulation device 126 will be slightly larger when inflated, as is illustrated in FIG. 4, and a gas filled insulation zone 138 will be formed between the outer surface of the catheter body 102 and the inner surface of the insulation device.

Figure 7:
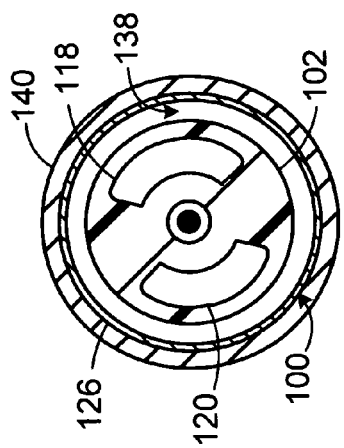
FIG. 7 is a section view take along line 7-7 in FIG. 5.
Figure 5:
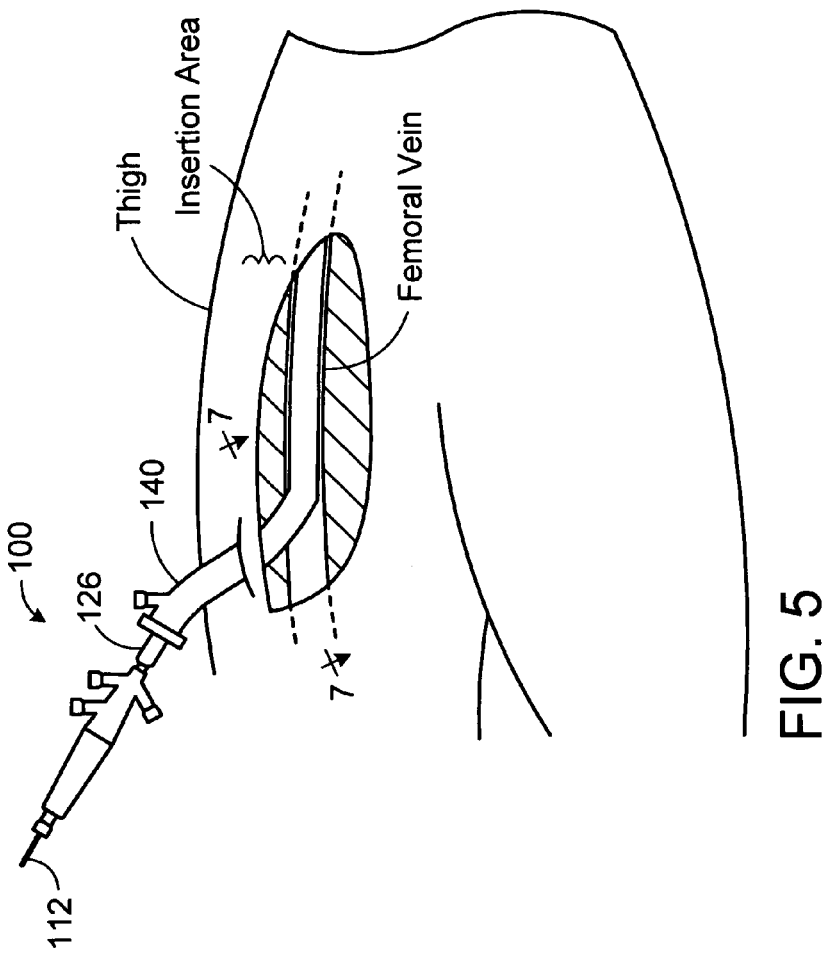
FIG. 5 is a cutaway view showing the probe illustrated in FIG. 1 being inserted into the femoral vein in the thigh of a patient.

One exemplary method of deploying the catheter 100 and using super-cooled fluid to create a lesion is illustrated in FIGS. 5-7. The same deployment method would be used in a JT cooling based system. After the guidewire 112 has been advanced through the femoral vein and into the target pulmonary vein, a long, transseptal introducer sheath 140 may be advanced over the guidewire to a position adjacent to the pulmonary vein. The catheter 100 may then be advanced through the sheath 140 and over the guidewire 112 with the cryogenic element 104 and inflatable insulation device 126 deflated. After the deflated cryogenic element 104 has been positioned adjacent to the pulmonary vein, it will be inflated with room temperature perfluorocarbon and advanced into contact with the pulmonary vein ostium. Alternatively, the cryogenic element 104 may be advanced into contact with the ostium prior to inflation with room temperature perfluorocarbon. The inflatable insulation device 126 will then be inflated, preferably with a gas such as $CO_2$ that can be readily absorbed by the body in the event of a leak, to a pressure of about 1-3 atmospheres. This may be accomplished by hand with a syringe or through the use of an automated device that would supply a suitable amount of gas. In either case, the pressure within the inflatable insulation device 126 may be monitored to detect leaks. The gas within the insulation device 126 will insulate tissue from super-cooled fluid within the catheter body 102 during the lesion formation procedure. Super-cooled fluid may then be circulated through the cryogenic element 104 by way of the infusion and ventilation lumens 118 and 120 for prescribed freezing periods (e.g. 60 to 180 seconds) to form the lesion. In addition to insulating tissue from the super-cooled fluid and increasing the thermal efficiency of the overall system, the inflatable insulation device 126 will engage the inner surface of the introducer sheath 140 (FIG. 7) and prevent the catheter body 102 from moving during the procedure. Once the cryogenic procedure has been completed, the cryogenic element 104 and inflatable insulation device 126 will be deflated and the catheter 100 removed from the patient.

The present inventions are not limited to any particular dimensions and materials. Nevertheless, the materials and dimensions of an exemplary implementation of the catheter 100 that is well suited for the isolation of pulmonary veins will be described for illustrative purposes. The exemplary catheter body 102 is preferably a multi-lumen extrusion formed from a flexible biocompatible thermoplastic material, such as a Pebax® material (polyether block emide). Suitable catheter lengths for cardiovascular applications range from about 80 cm to about 100 cm, although the length may be varied to suit the intended application. The outer diameter of the catheter body 102 will be about 3 mm to about 4 mm, while the diameter of the guidewire lumen 114 will be about 1 mm. The cross-sectional area of the infusion and ventilation lumens 118 and 120 should be equal so that the flow resistance to and from the cryogenic element 104 is equal. Here, the inflation pressure of the cryogenic element 104 will be one-half the pressure at the inlet of the infusion lumen 118. The exemplary cryogenic element 104, which is an inflatable structure that is intended occlude a pulmonary vein and form a therapeutic lesion around the pulmonary vein ostium, will be about 15 mm to about 30 mm in diameter when inflated.

Turning to the inflatable insulation device 126 in the exemplary implementation, suitable materials include Nylon 12 or Pebax® with a wall thickness of about 0.025 to about 0.075 mm. The proximal end of the inflatable insulation device 126 will be about 1 cm to about 20 cm from the distal end of handle 110 (or the distal end of the strain relief element in those instances where a strain relief element is employed), which corresponds to a non-working length of about 2 cm to about 25 cm. It should be noted here that an insertion area for the catheter 100 will typically be about 1 cm to about 5 cm, measured from the skin to the vein, because physicians will insert the catheter at an acute angle. The distal end of the exemplary insulation device 126 will be about 2 cm to about 40 cm from the cryogenic element 104. The outer diameter of the inflatable insulation device 126 will be about 0.3 mm to about 1.0 mm larger than the outer diameter of the catheter body 102 (i.e. about 3.3 mm to 5 mm depending on the diameter of the catheter body) when inflated. Typically, about 3-5 ml of gas will be used to inflate the insulation device 126. When deflated, the outer diameter of the inflatable insulation device 126 will be only slightly greater than that of the catheter body 102. An inflatable insulation device 126 with a 0.05 mm wall thickness, for example, will have an outer diameter that is only about that is only about 0.15 mm greater than the diameter of the catheter body 102.

The exemplary catheter 100 may be reconfigured in a variety of ways. For example, the catheter body 102 could be a steerable catheter body with steering wires connected to a steering control on the handle 110. Another alternative would be to replace the exemplary inflatable cryogenic element 104 with a hollow metal tip. With respect to insulation, the length inflatable insulation device 126 could be reduced such that it only extends over the small portion of the working length 130 that will be aligned with tissue in the insertion area. Such an inflatable insulation device 126 could, for example, extend from about an area just proximal of the distal end of the non-working length to an area just distal of the insertion area. In the context of a catheter 100 that has a 10 cm long non-working length and is intended to be inserted into the femoral vein, the proximal end of the inflatable insulation device 126 would be about 2 cm to about 8 cm from the distal end of the handle 110, while the distal end of the inflatable insulation device would be about 20 cm to about 30 cm from the distal end of the handle.

III. Exemplary Insulated Introducer Sheath

An introducer sheath 200 in accordance with a preferred embodiment of a present invention is illustrated in FIGS. 8-10. The illustrated embodiment includes a elongate sheath body 202 with a proximal portion 208 that is secured to a handle 210. An inflatable insulation device 226 is carried on the exterior surface of the sheath body 202. The inflatable insulation device 226 preferably extends distally from a location in close proximity to the distal end of the handle 210, over the non-working length 228 of the sheath body 202 and along at least the proximal area of the working length 230. This will insure that a portion of the inflatable insulation device 226 will be coextensive with the insertion area during use. In the exemplary embodiment, the inflatable insulation device 226 extends from a location in close proximity to the handle 210 to the distal portion 206 the sheath body 202. This would typically be about 2 mm to about 3 mm from the distal end of the handle 210. The distal end of the inflatable insulation device 226 will preferably be about 2 mm to about 3 mm from the distal end of the sheath body 202 so there will be "end to end" insulation.

The sheath body 202, which should be lubricious to reduce friction during movement of a catheter through the sheath, may be advanced into position over a guidewire or steerable catheter in conventional fashion. Alternatively, the sheath may be provided with its own steering mechanisms. The materials and dimensions will depend on the intended application. In cardiovascular applications, for example, the proximal portion 208 of the sheath body 202 is preferably formed from a Pebax® and stainless steel braid composite and the distal portion 206 is preferably formed from a more flexible material, such as unbraided Pebax®. The length of the sheath body 202 will typically range from about 60 cm to about 110 cm, the outer diameter will typically be about 3 mm to about 5 mm and the inner diameter will typically be about 2.3 mm to about 4 mm.

The inflatable insulation device 226 illustrated in FIGS. 8-10 is substantially similar to the inflatable insulation device 126 described above with reference to FIGS. 1-7 and the discussion in Section II above is applicable to the insulation device 226. For example, the inflatable insulation device 226 may be formed by securing a tubular length of material to the exterior of the sheath body 202 with thermal bonding or adhesive bonding (depending on materials) and anchors 232 may be provided to prevent leakage. Gas may be infused and ventilated by way of a small tube 234, which is carried on the exterior of the sheath body 202 and connected to a gas port 236 on the handle 210. When inflated, a gas filled insulation zone 238 will be formed between the outer surface of the sheath body 202 and the inner surface of the insulation device 226.

The exemplary sheath 200 has a wide variety of applications. In the context of lesion formation procedures which involve the use of a catheter with a cryogenic element at or near the distal tip, the sheath 200 may be used to guide the catheter to the target tissue area and to protect non-target tissue, including the tissue in the insertion area, from the damage. When creating a pulmonary vein lesion with super-cooled fluid, for example, the sheath 200 may be advanced over a guidewire through the femoral vein and into position adjacent to the target pulmonary vein with the inflatable insulation device 226 deflated. The catheter may then be advanced through the sheath 200 with the cryogenic element deflated. After the deflated cryogenic element has been positioned adjacent to the pulmonary vein, it will be inflated with room temperature perfluorocarbon and advanced into contact with the pulmonary vein ostium. Alternatively, the cryogenic element may be advanced into contact with the ostium prior to inflation with room temperature perfluorocarbon. After the inflatable insulation device 226 has been inflated, preferably with a gas such as $CO_2$ in the manner described in Section II above, the lesion formation procedure may begin. The gas within the insulation device 226 will insulate tissue from the extremely low temperatures associated with the catheter body as super-cooled fluid is circulated through the cryogenic element during the lesion formation procedure. The cryogenic element and inflatable insulation device 226 may be deflated after the lesion formation procedure is complete so that the catheter and sheath may be removed from the patient.

IV. Exemplary Insulated Surgical Probe

Figure 11:
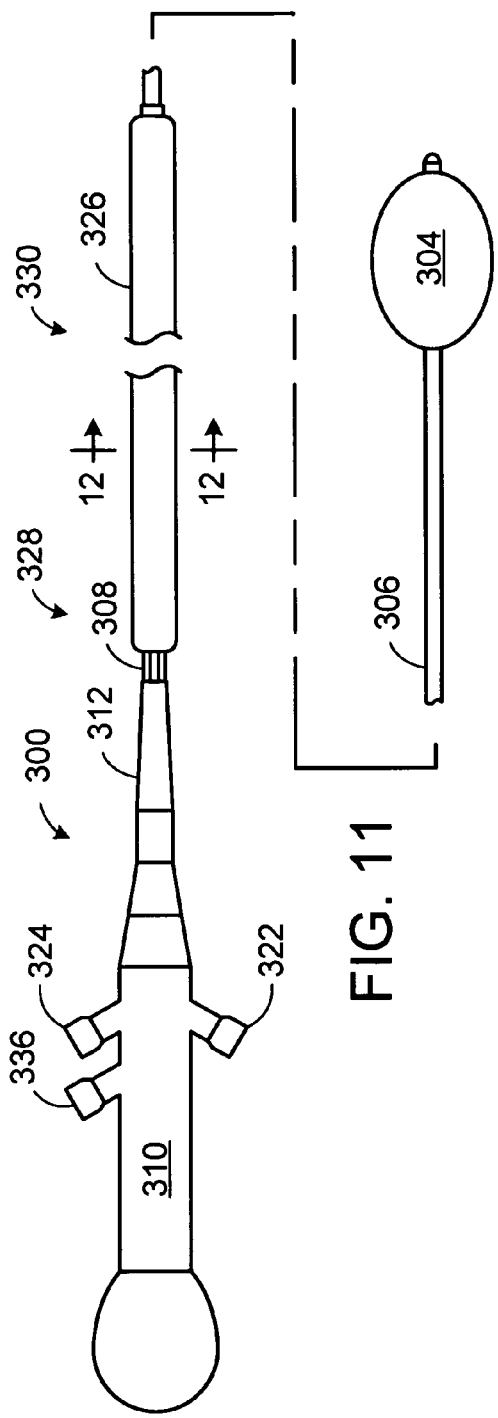
FIG. 11 is a plan view of a probe in accordance with a preferred embodiment of a present invention.
Figure 13:
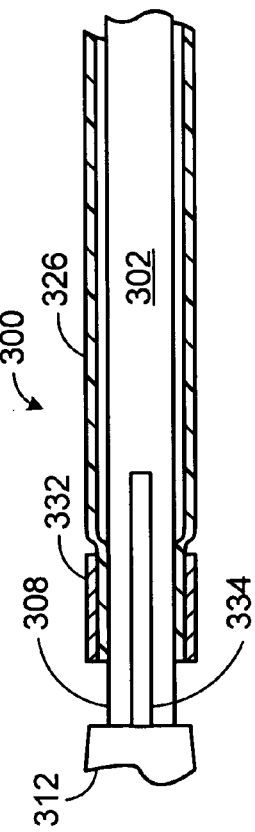
FIG. 13 is an enlarged, partial section view of a portion of the probe illustrated in FIG. 11.
Figure 12:
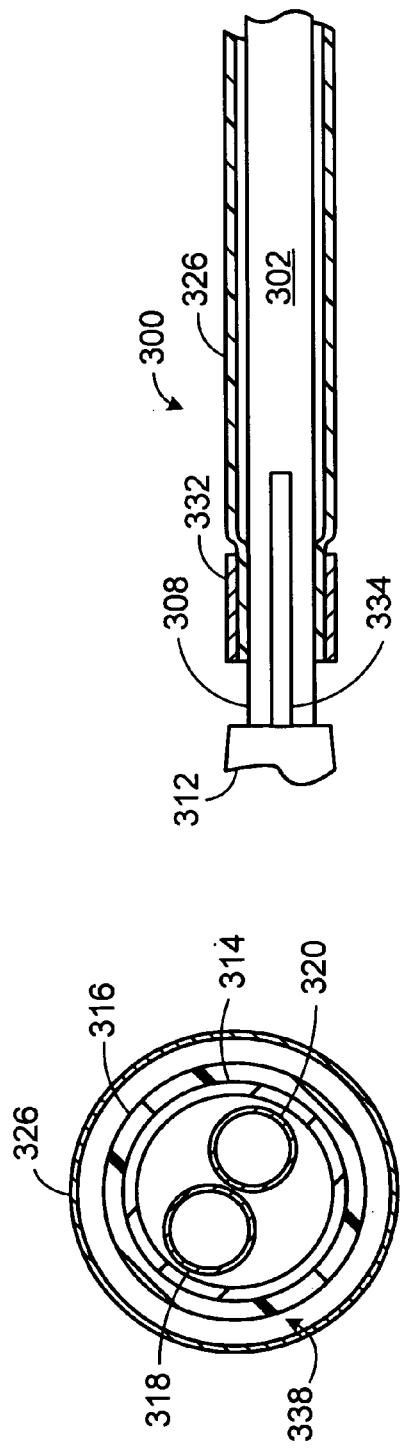
FIG. 12 is a section view taken along line 12-12 in FIG. 11.

A surgical probe 300 in accordance with one embodiment of a present invention is illustrated in FIGS. 11-13. The exemplary surgical probe 300 includes a relatively short shaft 302 and an inflatable cryogenic element 304 carried on the distal portion 306 of the shaft. The proximal portion 308 of the shaft 302 is secured to a handle 310. A strain relief element 312 is also provided. The shaft 302 will typically be about 10 cm to about 45 cm in length and will also typically be relatively stiff. In other words, the shaft is either rigid, malleable, or somewhat flexible. A rigid shaft cannot be bent. A malleable shaft is a shaft that can be readily bent by the physician to a desired shape, without springing back when released, so that it will remain in that shape during the surgical procedure. Thus, the stiffness of a malleable shaft must be low enough to allow the shaft to be bent, but high enough to resist bending when the forces associated with a surgical procedure are applied to the shaft. A somewhat flexible shaft will bend and spring back when released. However, the force required to bend the shaft must be substantial. The exemplary shaft 302 consists of a malleably hypotube 314 with an outer polymer jacket 316. The proximal portion 308 is, however, stiffer than the distal portion 306. The proximal portion 308 is also longer than the distal portion 306 in the exemplary embodiment.

Infusion and ventilation lumens 318 and 320 for the cooling fluid extend through the shaft 302. The distal ends of the infusion and ventilation lumens 318 and 320 terminate at respective openings (not shown) on the exterior surface of the shaft 302 that are located within the cryogenic element 304. The proximal ends of the infusion and ventilation lumens 318 and 320 are connected to infusion and ventilation ports 322 and 324 on the handle 310.

An inflatable insulation device 326 is carried on the exterior surface of the shaft 302 in the exemplary embodiment illustrated in FIGS. 11-13. The inflatable insulation device 326 preferably extends distally from a location in close proximity to the distal end of the strain relief element 312 (or the handle 310 if there is no strain relief element), over the non-working length 328 of the shaft 302 and along at least the proximal area of the working length 330. This will insure that a portion of the inflatable insulation device 326 will be coextensive with the insertion area during use. In the exemplary embodiment, the inflatable insulation device 326 extends from a location in close proximity to the strain relief element 312 and over the proximal portion 308 the shaft 302. This would typically be about 1 cm to about 10 cm from the distal end of the strain relief element 312, which corresponds to a non-working length of about 2 cm to about 15 cm.

The inflatable insulation device 326 illustrated in FIGS. 11-13 is substantially similar to the inflatable insulation device 126 described above with reference to FIGS. 1-7 and the discussion in Section II above is applicable to the insulation device 326. For example, the inflatable insulation device 326 may be formed by securing a tubular length of material to the exterior of the shaft 302 with thermal bonding or adhesive bonding (depending on materials) and anchors 332 may be provided to prevent leakage. Gas may be infused and ventilated by way of a small tube 334, which is carried on the exterior of the shaft 302 and connected to a gas port 336 on the handle 310. When inflated, a gas filled insulation zone 338 will be formed between the outer surface of the shaft 302 and the inner surface of the insulation device 326.

The exemplary surgical probe 300 may be used in wide variety of procedures that employ super-cooled fluid, or the JT effect, for therapeutic purposes. For example, surgical probe 300 may be introduced into a target location, such as within a cancerous tumor, using laparoscopic techniques. Here, the surgical probe 300 may be introduced with a trocar, radially expandable port, or step trocar expandable port. The exemplary surgical probe 300 may also be used to create endocardial and epicardial lesions where access to the heart is obtained by way of a thoracostomy. In either case, and in the context of a super-cooled fluid system, the cryogenic element 304 and insulation device 326 will be deflated when the working portion of the probe 300 is inserted into the patient. After the deflated cryogenic element 304 has been positioned at or within the target tissue region, it will be inflated with room temperature perfluorocarbon. The inflatable insulation device 326 will then be inflated to insulate tissue from super-cooled fluid that will subsequently flow through the shaft 302 during the therapeutic procedure. Once the procedure has been completed, the cryogenic element 304 and inflatable insulation device 326 will be deflated and the probe 300 removed from the patient.

The exemplary surgical probe 300 may be reconfigured in a variety of ways. For example, the shaft distal portion 306 could be steerable and controlled by steering wires that extend from the distal tip to a steering control on the handle 310. Another alternative would be to replace the exemplary inflatable cryogenic element 304 with a hollow metal tip. With respect to insulation, the length inflatable insulation device 326 could be reduced such that it only extends over the small portion of the working length 330 that will be aligned with tissue in the insertion area. Such an inflatable insulation device 326 could, for example, extend from about an area just proximal of the distal end of the non-working length to an area just distal of the insertion area. In the context of a surgical probe 300 that has a 5 cm long non-working length and is intended to be inserted into the chest through the use of a thoracostomy, the proximal end of the inflatable insulation device 326 would be about 1 cm to about 3 cm from the distal end of the strain relief element 312 (or the handle 310 if there is no strain relief element), while the distal end of the inflatable insulation device would be about 20 cm to about 30 cm from the distal end of the handle.

V. Exemplary Insulated Introducer Ports

Figure 15:
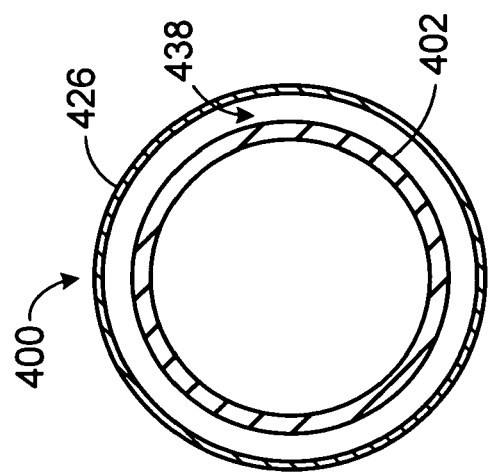
FIG. 15 is a section view take along line 15-15 in FIG. 14.
Figure 14:
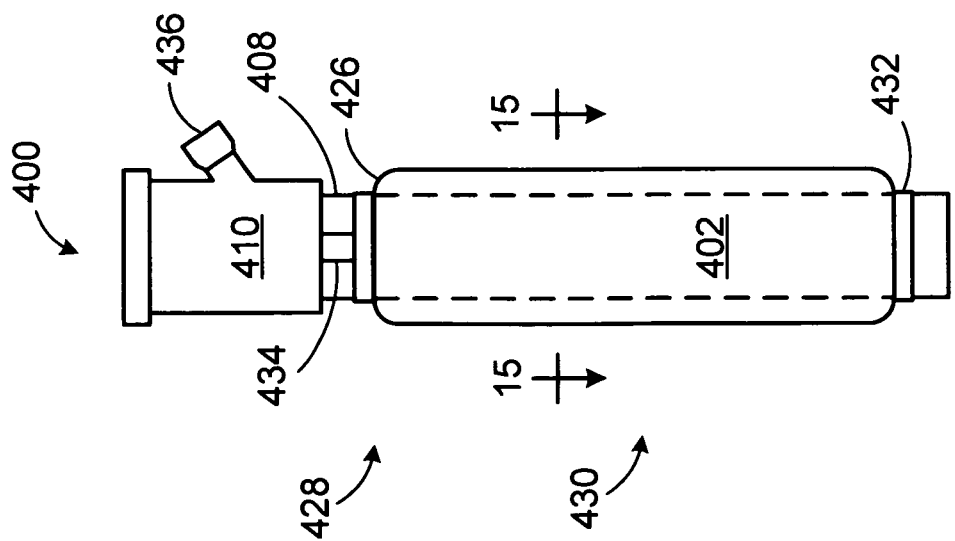
FIG. 14 is a front view of an introducer port in accordance with a preferred embodiment of a present invention.

An introducer port 400 in accordance with one embodiment of a present invention is illustrated in FIGS. 14 and 15. The illustrated embodiment includes an introducer tube 402 with a proximal portion 408 that is secured to a handle 410. An inflatable insulation device 426 is carried on the exterior surface of the introducer tube 402. The inflatable insulation device 426 preferably extends distally from a location in close proximity to the distal end of the handle 410, over the non-working length 428 of the introducer tube 402 and along at least the proximal area of the working length 430. This will insure that a portion of the inflatable insulation device 426 will be coextensive with the insertion area during use. In the exemplary embodiment, the inflatable insulation device 426 extends from a location in close proximity to the handle 410 to the distal portion 406 the introducer tube 402. This would typically be about 2 mm to about 3 mm from the distal end of the handle 410 to about 2 mm to about 3 mm from the distal end of the introducer tube 402 so that "end to end" insulation is provided.

The introducer port 400 may be used, for example, to introduce catheters and surgical probes into the body. The materials and dimensions of the introducer tube 402 will depend on the intended application. In cardiovascular applications, for example, the introducer tube 402 is preferably formed from polyethylene and its length will typically range from about 5 cm to about 20 cm, the outer diameter will typically be about 3 mm to about 6 mm and the inner diameter will typically be about 2.3 mm to about 5 mm.

The inflatable insulation device 426 illustrated in FIGS. 14 and 15 is substantially similar to the inflatable insulation device 126 and the discussion in Section II above is applicable to the insulation device 426. For example, the inflatable insulation device 426 may be formed by securing a tubular length of material to the exterior of the introducer tube 402 with thermal bonding or adhesive bonding (depending on materials) and anchors 432 may be provided to prevent leakage. Gas may be infused and ventilated by way of a small tube 434, which is carried on the exterior of the introducer tube 402 and connected to a gas port 436 on the handle 410. When inflated, a gas filled insulation zone 438 will be formed between the outer surface of the introducer tube 402 and the inner surface of the insulation device 426.

Figure 17:
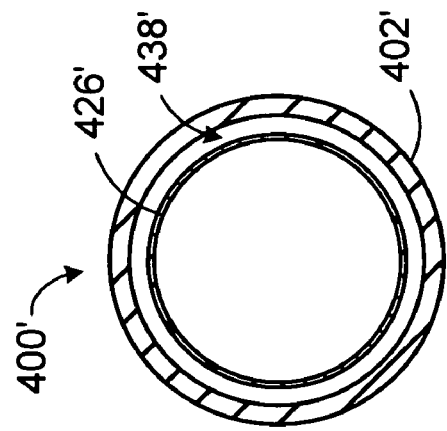
FIG. 17 is a section view take along line 17-17 in FIG. 16.
Figure 16:
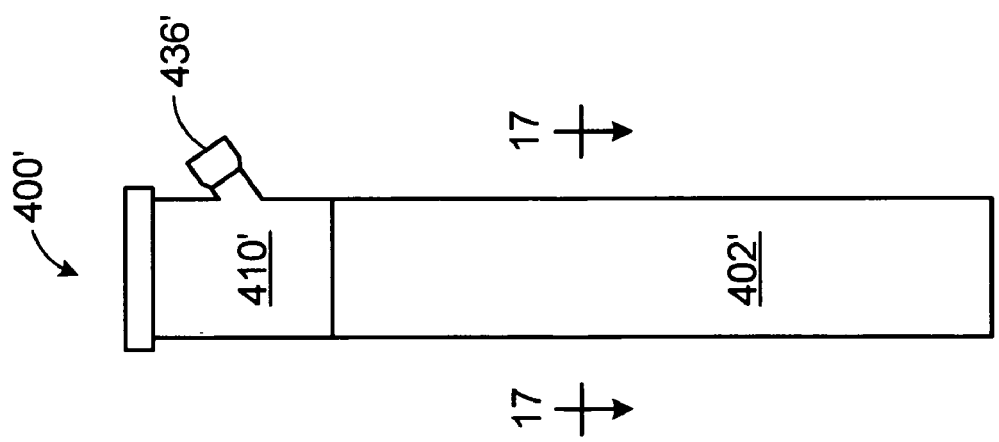
FIG. 16 is a front view of an introducer port in accordance with a preferred embodiment of a present invention.

Another exemplary introducer port, which is generally represented by reference numeral 400' in FIGS. 16 and 17, is substantially similar to introducer port 400. Here, however, introducer tube 402' has a slightly larger inner and outer diameter and the inflatable insulation device 426' is located within the introducer tube. The handle 410' includes a gas port 436' that may be connected to the interior of the inflatable insulation device 426' by a tube (not shown). When inflated, a gas filled insulation zone 438' will be formed between the inner surface of the introducer tube 402' and the surface of the insulation device 426' that faces the tube.

The introducer ports 400 and 400' have a wide variety of applications. In the context of lesion formation procedures which involve the use of a catheter or surgical probe with a distal cryogenic element, the introducer ports 400 and 400' may be used to provide access to interior regions of the patient's body as well as to protect non-target tissue, including the tissue in the insertion area, from damage. More specifically, a cryogenic catheter or surgical probe may be inserted through the introducer port 400 (or 400') with the insulation device 426 (or 426') and cryogenic element deflated. Once the catheter or surgical probe has been positioned at the target tissue region, the cryogenic element may be inflated with room temperature perfluorocarbon. Next, the inflatable insulation device 426 (or 426') will be inflated to insulate tissue from the super cool temperatures associated with the catheter body or surgical probe shaft during the lesion formation procedure. Next, super-cooled fluid will be circulated through the cryogenic element for prescribed freezing periods. Once the procedure has been completed, the cryogenic element and inflatable insulation device 426 (or 426') will be deflated so that the catheter or surgical probe may be removed from the patient.

VI. Exemplary Trocars

A trocar 500 in accordance with one embodiment of a present invention is illustrated in FIGS. 18 and 19. The illustrated embodiment includes a trocar sleeve 502 with a proximal portion that is secured to a handle 510. An inflatable insulation device 526 is carried on the interior surface of the trocar sleeve 502. The inflatable insulation device 526 preferably extends distally from a location in close proximity to the distal end of the handle 510 to the proximal end of the sharpened sleeve area 503. This will insure that a portion of the inflatable insulation device 526 will be coextensive with the insertion area during use. This would typically be about 2 mm to about 3 mm from the distal end of the handle 510 to about 2 mm to about 3 mm from the distal end of the trocar sleeve 402 so that "end to end" insulation is provided.

The trocar 500 may be used, for example, to introduce surgical devices into the body. The materials and dimensions of the trocar sleeve 502 will depend on the intended application. The trocar sleeve 502 is preferably formed from stainless steel and its length will typically range from about 3 cm to about 8 cm, the outer diameter will typically be about 16 mm to about 32 mm and the inner diameter will typically be about 15 mm to about 30 mm. The inflatable insulation device 526 illustrated in FIGS. 18 and 19 is substantially similar to the inflatable insulation device 126 and the discussion in Section II above is applicable to the insulation device 526. For example, the inflatable insulation device 526 may be formed by securing a tubular length of material to the interior of the trocar sleeve 502 with adhesive bonding. Gas may be infused and ventilated by way of a small tube (not shown), which is carried on the interior of the trocar sleeve 502 and connected to a gas port 536 on the handle 510. When inflated, a gas filled insulation zone 538 will be formed between the inner surface of the trocar sleeve 502 and the surface of the insulation device 526 that faces the tube. The cross-sectional size of the gas filled insulation zone 538 when inflated, i.e. percentage of the sleeve lumen that is occluded, will depend on the intended application and can vary from a small percentage to near complete occlusion.

The trocar 500 has a wide variety of applications. In the context of lesion formation procedures which involve the use of a surgical probe with a distal cryogenic element, the trocar 500 may be used to provide access to interior regions of the patient's body as well as to protect non-target tissue, including the tissue in the insertion area, from damage. More specifically, a cryogenic surgical probe may be inserted through the trocar 500 with the insulation device 526 and cryogenic element deflated. Once the surgical probe has been positioned at the target tissue region, the cryogenic element may be inflated with room temperature perfluorocarbon. Next, the inflatable insulation device 526 will be inflated to insulate tissue from the super cool temperatures associated with the surgical probe shaft during the lesion formation procedure. Next, super-cooled fluid will be circulated through the cryogenic element for prescribed freezing periods. Once the procedure has been completed, the cryogenic element and inflatable insulation device 526 will be deflated so that the surgical probe may be removed from the patient.

It should be noted that trocars in accordance with the present inventions are not limited to those which employ the angled sharpened sleeve area 503 illustrated in FIG. 18. For example, and turning to FIGS. 20 and 21, a trocar sleeve 502' is shown with a sharpened sleeve area 503' that is generally perpendicular to the longitudinal axis of the sleeve. The sleeve 502' may be substituted for the sleeve 502 in the trocar 500.

Although the present inventions have been described in terms of the preferred embodiments above, numerous modifications and/or additions to the above-described preferred embodiments would be readily apparent to one skilled in the art. Additionally, the scope of the inventions includes any combination of the elements from the various species and embodiments disclosed in the specification that are not already described. It is intended that the scope of the present inventions extend to all such modifications and/or additions and that the scope of the present inventions is limited solely by the claims set forth below.

I claim:

1. A device for forming lesions in a pulmonary vein after passing through an insertion area in the patient's thigh, the device comprising:
    a shaft defining a proximal region, a distal region, at least one lumen and a length sufficient to extend from a pulmonary vein, into the femoral vein, and through the insertion area in the patient's thigh;
    a lesion formation device associated with the distal region of the shaft, configured to form a lesion in the pulmonary vein and operably connected to the lumen; and
    an inflatable insulation device carried by the shaft;
    wherein the lesion formation device and the inflatable insulation device are located on the shaft such that the inflatable insulation device will be located within the insertion area in the patient's thigh when the lesion formation device abuts the pulmonary vein.

2. A device as claimed in claim 1, further comprising:
    a handle associated with the proximal region of the shaft.

3. A device as claimed in claim 1, wherein the shaft comprises a catheter body.

4. A device as claimed in claim 1, wherein the shaft defines an exterior and the inflatable insulation device is carried on the exterior of the shaft.

5. A device as claimed in claim 1, wherein the inflatable insulation device defines an inflated diameter and a deflated diameter and the inflated diameter is greater than the deflated diameter.

6. A device as claimed in claim 1, wherein the inflatable insulation device extends from the proximal region of the shaft to the distal region.

7. A device as claimed in claim 1, wherein the shaft and the inflatable insulation device define respective proximal ends and the proximal end of the inflatable insulation device is located in close proximity to the proximal end of the shaft.

8. A device as claimed in claim 1, wherein the shaft defines a proximal end, the device further comprising:
a handle associated with the proximal end of the shaft;
wherein the inflatable insulation device defines a proximal end and the proximal end of the inflatable insulation device is located in close proximity to the handle.

9. A device for forming lesions in a pulmonary vein after passing through an insertion area in the patient's thigh, the device comprising:
a shaft defining a proximal region, a distal region, at least one lumen and a length sufficient to extend from a pulmonary vein, into the femoral vein, and through the insertion area in the patient's thigh;
a lesion formation device associated with the distal region of the shaft, configured to form a lesion in the pulmonary vein and operably connected to the lumen; and
means, associated with the shaft, for inflating and thermally insulating the insertion area in the patient's thigh from the shaft when the lesion formation device abuts the pulmonary vein.

10. A device as claimed in claim 9, further comprising:
a handle associated with the proximal region of the shaft.

11. A device as claimed in claim 9, wherein the shaft comprises a catheter body.

12. A device as claimed in claim 9, wherein the shaft defines an exterior and the inflatable insulation device is carried on the exterior of the shaft.

13. A device as claimed in claim 9, wherein the shaft and the means for inflating and thermally insulating the insertion area define respective proximal ends and the proximal end of the means for inflating and thermally insulating the insertion area is located in close proximity to the proximal end of the shaft.

14. A device as claimed in claim 9, wherein the shaft defines a proximal end, the device further comprising:
a handle associated with the proximal end of the shaft;
wherein the means for inflating and thermally insulating the insertion area defines a proximal end and the proximal end of the means for inflating and thermally insulating the insertion area is located in close proximity to the handle.

* * * * *